United States Patent

Flohr

[11] Patent Number: 6,047,039
[45] Date of Patent: Apr. 4, 2000

[54] METHOD FOR POST-PROCESSING OF A TOMOGRAM, AND COMPUTED TOMOGRAPHY APPARATUS OPERATING IN ACCORDANCE WITH THE METHOD

[75] Inventor: Thomas Flohr, Uehlfeld, Germany

[73] Assignee: Siemens Aktiengesellschaft, Munich, Germany

[21] Appl. No.: 09/137,156

[22] Filed: Aug. 20, 1998

[30] Foreign Application Priority Data

Aug. 20, 1997 [DE] Germany .......................... 197 36 241

[51] Int. Cl.[7] ....................................... A61B 6/03
[52] U.S. Cl. ................................. 378/4; 378/901
[58] Field of Search ................... 378/4, 98, 12, 378/901; 382/131

[56] References Cited

U.S. PATENT DOCUMENTS 5,416,815  5/1995  Hsieh ........................................... 378/4
5,802,135  9/1998  Wohlrab ....................................... 378/4

OTHER PUBLICATIONS

A Review of Physical Aspects of X–ray Transmission Computed Tomography, Webb, IEE Proceedings, vol. 134, Part A, Feb., 1987, pp. 126–135.

*Primary Examiner*—David V. Bruce
*Attorney, Agent, or Firm*—Hill & Simpson

[57] ABSTRACT

In a method for operating a third-generation computed tomography apparatus and in a computed tomography apparatus operating according to this method, ring artefacts are removed. The pixel values of the tomogram are subjected to one or more median filterings and to an averaging. The median filterings and the averaging take place along a number of processing directions.

4 Claims, 3 Drawing Sheets

METHOD FOR POST-PROCESSING OF A TOMOGRAM, AND COMPUTED TOMOGRAPHY APPARATUS OPERATING IN ACCORDANCE WITH THE METHOD

BACKGROUND OF THE INVENTION

1. Field of the Invention

The present invention relates to a method for operating a computed tomography (CT) apparatus for the post-processing of a tomogram, as well as to a computed tomography apparatus operating according to such a method.

2. Description of the Prior Art

Due to differential deviations of the individual measurement system channels of a computed tomography apparatus from the respective calibration state, ring artefacts arise in the tomograms of CT apparatuses of the third generation, these artefacts being centered around the center of rotation of the apparatus. This problem is described in IEEE Proceedings, Vol. 134, Part A, February 1987, pages 126–135.

SUMMARY OF THE INVENTION

An object of the present invention is to provide a computed tomography apparatus of the type third generation and a method for operating same wherein a correction of the ring artefacts described above, by means of an image post-processing, takes place in the reconstructed tomograms.

The above object is achieved in accordance with the principles of the present invention in a method for operating a computed tomography apparatus, and a computed tomography apparatus operating according to the method, wherein an image matrix is obtained and all bone and air portions in this matrix are masked, the resulting masked image is subjected to a median filtering along a number of straight processing lines all proceeding through the center of rotation of the computed tomography apparatus, and which cover the masked image matrix so that each pixel thereof lies on one of the straight processing lines. A median-filtered image thereby results, and a difference image is then formed by subtracting this median-filtered image from the masked image. The difference image is then subjected to a threshold operation to obtain an intermediate image, and the intermediate image is low-pass filtered by simple averaging. The resulting low-pass image is then subtracted from the original, starting image, so that a final image is obtained which is free of ring artifacts.

In a further version of the invention, in a method for operating a computed tomography apparatus and a computed tomography apparatus operating according to the method, a further median filtering is undertaken. This further median filtering is conducted in a further difference image, which is formed from the aforementioned masked image and the aforementioned intermediate image. Yet another difference image is then formed by subtracting the further median filtered image from the masked image, and it is this yet further different image which is then subjected to the low-pass filtering.

In the inventive method and apparatus, the detection of the ring artefacts takes place by median filtering in the radial direction. In this way, ring artefacts are completely corrected, rather than being merely reduced in their amplitude and blurred. In addition, in contrast to known methods, disturbing bone structures in the image are eliminated before the median filtering, by a simple threshold operation.

DESCRIPTION OF THE PREFERRED EMBODIMENTS

Figure 1:
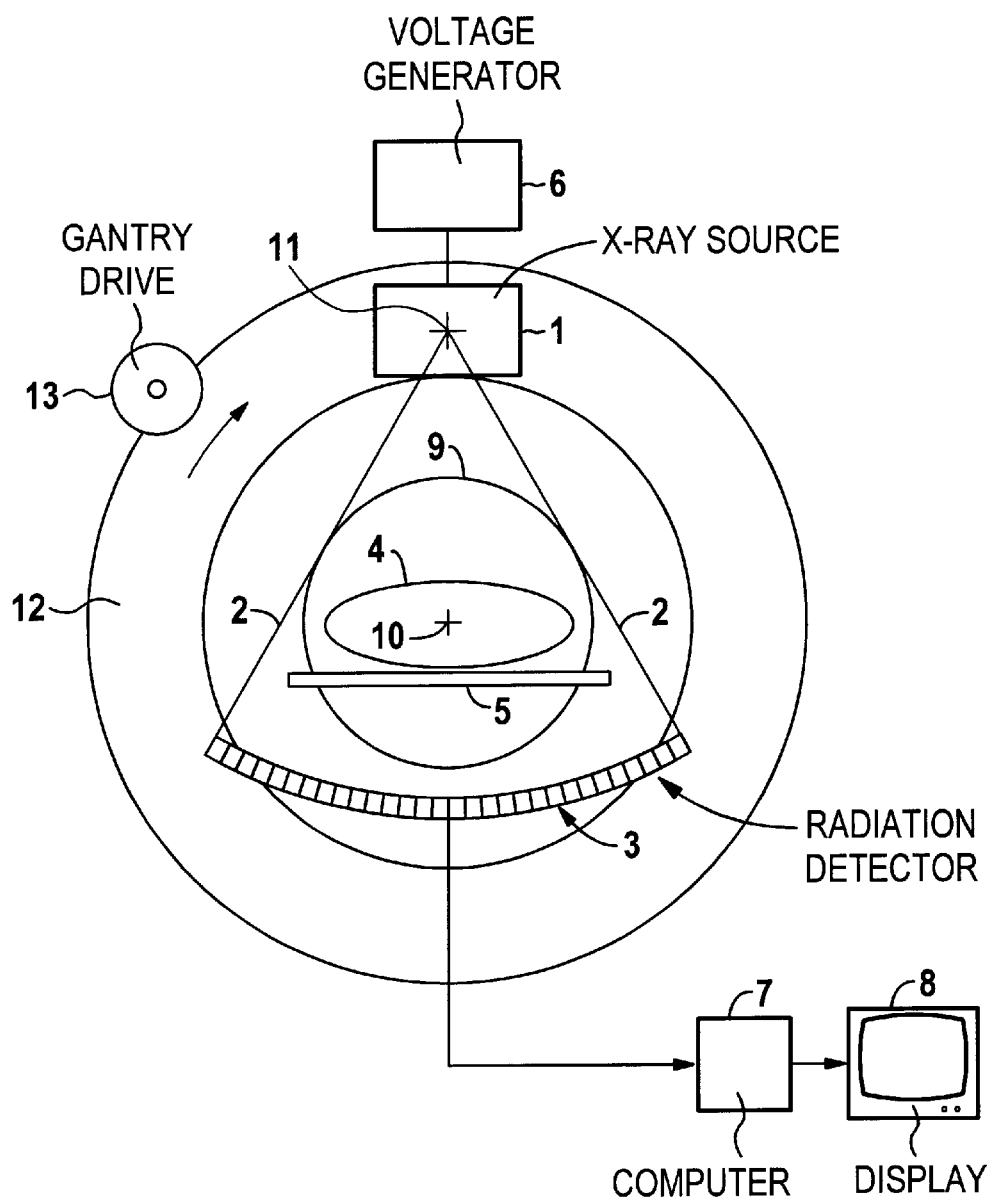
FIG. 1 is a schematic illustration showing the basic components of a computed tomography apparatus of the third generation.
Figure 2:
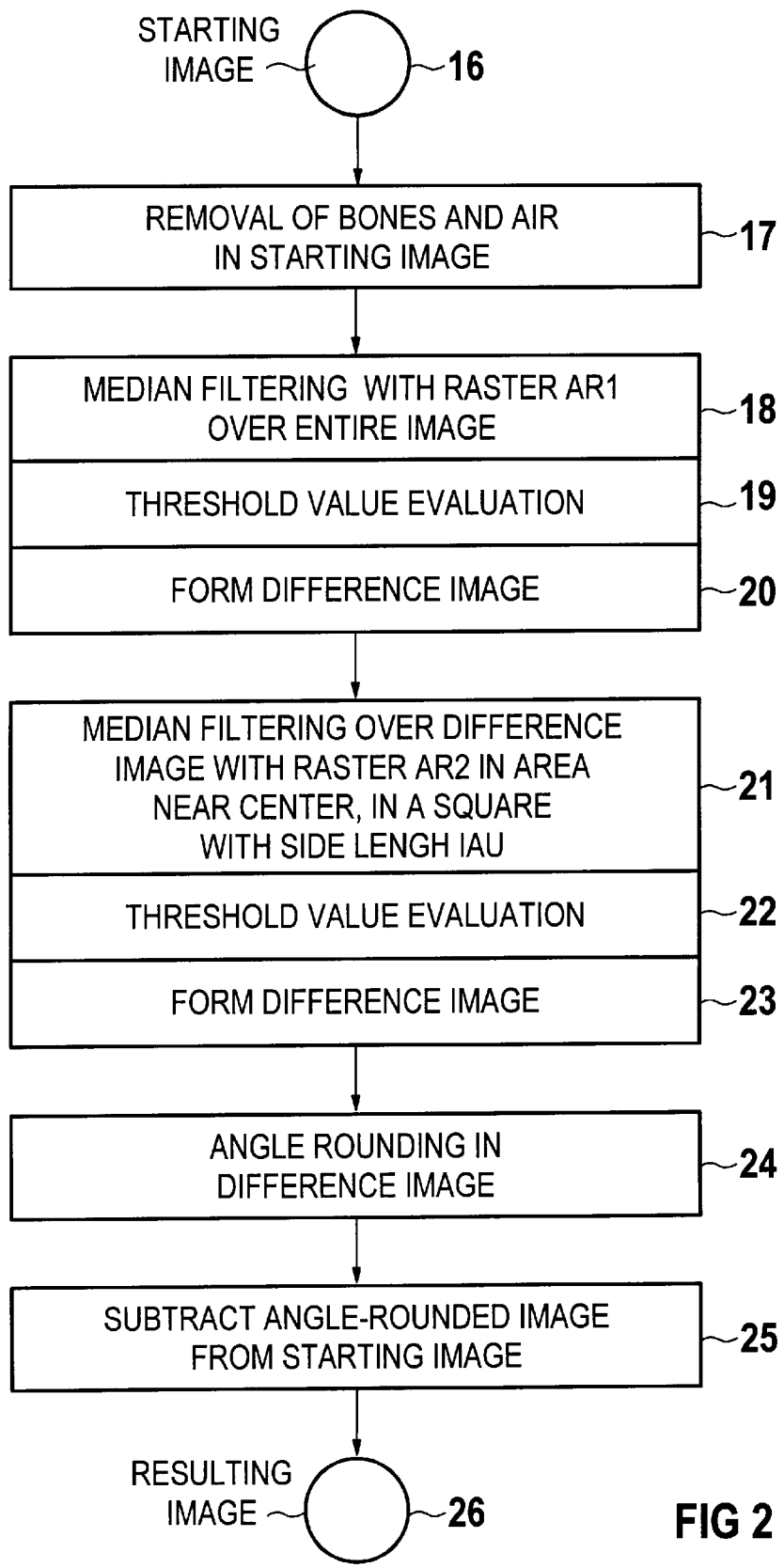
FIG. 2 shows the basic computing steps for the computed tomography apparatus according to FIG. 1.

The third generation computed tomography apparatus shown in FIG. 1 has a known arrangement of components which also represents the inventive apparatus, except the programming and operation of the computer 7 are not convention, and proceed in accordance with the inventive method described below. The CT apparatus of FIG. 1 includes a measurement unit formed by an X-ray source 1 that emits a fan-shaped X-ray beam 2 and a detector 3 having a series of individual detectors, e.g. 512 individual detectors. The focus of the X-ray source is designated 11. The patient 4 to be examined lies on a patient table 5. For the scanning of the patient 4, the measurement unit 1, 3 is rotated through 360° by a gantry 12 which is moved by a drive 13 around a measurement field 9 in which the patient 4 is located. The axis of rotation is designated 10. The X-ray source 1, which is fed by a voltage generator 6, is operated in pulsed fashion or with continuous radiation emission. At predetermined angular positions of the measurement unit 1, 3, sets of data are produced that are supplied by the detector 3 to the computer 7, which calculates from the produced data sets the attenuation coefficients of predetermined image points and graphically reproduces them on a display 8. An image of the transilluminated slice of the patient accordingly appears on the display apparatus In FIG. 2, the circle 16 schematically represents the input image which is to be processed (post-processing). In method steps 17–25, the following image processing steps take place successively:

Step 17 removal of bones and air in the image;
Step 18 median filtering with grid or raster AR1 over the entire image;
Step 19 threshold value evaluation;
Step 20 formation of a difference image;
Step 21 additional median filtering over the difference image with grid AR2 in an area near the center, in a square with side length IAU;
Step 22 threshold value evaluation;
Step 23 production of a difference image;
Step 24 angle rounding of the difference image;
Step 25 subtracting the angle-rounded difference image from the input image.

The circle 26 represents the resulting image.

In a CT image IBILD, there are $N_p \cdot N_p$ (e.g., 512·512) pixel values of the tomogram, generally as 12-bit integer values in the value range 0 . . . 4095 (Hounsfield scale), which are converted to the integer value scale –1024 to +3071 for the further image processing.

In the first processing step 17, bone and air portions in the image are eliminated, in order not to disturb later ring detection. For this purpose, all CT values greater than a particular threshold SWO (e.g., SWO=300) that could originate from bone structures are set equal to SWO. All CT values smaller than a determined threshold SWU that could originate from air or from air pockets are set equal to SWU (e.g., SWU=–300). The thresholds SWO and SWU are dependent both on the CT convolution Kernel used, i.e. the maximum sharpness of the CT reconstruction, and on the maximum attenuation value of the subject represented, and are e.g. determined empirically.

This method step 17 results in a new image matrix designated R1BILD, which likewise has $N_p \cdot N_p$ pixel values.

In processing steps 18–20, a correction image is produced in which the ring artefacts are isolated.

For this purpose, in the image matrix R1BILD a first median filtering is first conducted along a number of straight lines (radial lines) proceeding through the center of rotation 10 of the computed tomography apparatus. These straight lines cover the image matrix R1BILD such that each pixel lies on one of these straight lines. The first radial median filter has $2M_1+1$ support points (e.g., $M_1=2$) with spacing $a_{R1}$. The spacing $a_{R1}$ is approximately half as large as half the line width of a ring artefact, and is thus dependent both on the selected segment of the measurement field (zoom factor "zoom") and on the sharpness of the convolution Kernel used, and, given a small image segment, is larger than the pixel spacing in the radial direction. For each pixel P1 in the image R1BILD, the pixels with radial spacing $-M_1 a_{R1}$, $-(M_1+1) a_{R1}$, . . . , $(M_1-1) a_{R1}$, $M_1 a_{R1}$ are determined for example by means of nearest neighbor interpolation. Each pixel value P1 of the median-filtered image MED1BILD results from the median value Med1 of the pixel values of the $2M_1+1$ support points. The median value Med1 of $2M_1+1$ values is that value for which $M_1$ values are smaller or equally large, and the remaining $M_1$ values are greater or equally large. The median value of the five values 1, 4, 3, 8, 17, for example, is Med1=4. The first median filtering is shown schematically in FIG. 3.

After the first median filtering, the difference image DIFF1=R1BILD−MED1BILD is formed for all $N_p \cdot N_p$ pixels. The difference image DIFF1 should now contain only ring artefacts. In order to eliminate residual disturbing bone edges, etc., in the difference image DIFF1, a threshold operation with the artefact threshold $S_{art}$ is conducted. In this threshold operation, all pixel values in the difference image DIFF1 whose magnitude is greater than $S_{art}$ are identified as disturbances that were erroneously recognized as a ring. If they exceed $+S_{art}$, they are set equal to $+S_{art}$, and, if they lie below $-S_{art}$, they are set equal to $-S_{art}$. The artifact threshold $S_{art}$ depends on the selected CT convolution Kernel i.e. on the maximum sharpness of the CT image reconstruction, and is e.g. determined empirically. The difference image DIFF1 processed with the artefact threshold $S_{art}$ is called R2BILD.

In order to eliminate possible residual traces of ring artefacts with a different grid, for all pixel values $N_p \cdot N_p$, the difference image R3BILD is formed from the masked initial image R1BILD and the image R2BILD. Given ideal operation of the first median filter, R3BILD should no longer contain any ring artefacts. In R3BILD (or in a segment thereof) a second median filtering is now carried in method step 21, again along a multiplicity of straight lines (radial lines) proceeding through the center of rotation 10 of the computed tomography apparatus. These straight lines cover the image matrix in such a way that each pixel of the selected segment lies on one of these straight lines. The second radial median filter has $2M_2+1$ support points (e.g., $M_2=1$) with spacing $a_{R2}$ (e.g., $a_{R2}=a_{R1}/2$). The spacing $a_{R2}$ is dependent both on the selected segment of the measurement field (zoom factor) and also on the sharpness of the convolution Kernel used, and, given a small image segment, is greater than the pixel spacing in the radial direction. For each pixel P2 in the desired segment of the image R3BILD, the pixels with the radial spacing $-M_2 a_{R2}$, $-(M_2+1)a_{R2}$, . . . , $(M_2-1) a_{R2}$, $M_2 a_{R2}$ are determined e.g. by means of nearest neighbor interpolation. Each pixel value P2 of the median-filtered image MED2BILD results from the median value Med2 of the pixel values of the $2M_2+1$ support points.

After the second median filtering, a difference image DIFF2=R1BILD−MED2BILD is formed for all $N_p \cdot N_p$ pixels. In order to eliminate residual traces of disturbing bone edges etc., in the difference image DIFF2 a threshold operation with the artefact threshold $S_{art}$ is again conducted. In this threshold operation all pixel values in the difference image DIFF2 whose magnitude is greater than $S_{art}$ are identified as disturbances that were erroneously recognized as a ring. They are set equal to $+S_{art}$ or to $-S_{art}$ according to the procedure already described. The artifact threshold $S_{art}$ is e.g. determined empirically, and, as mentioned, depends on the selected CT convolution Kernel, i.e. on the maximum sharpness of the CT image reconstruction. The difference image DIFF2 processed with the artefact threshold $S_{art}$ is called R4BILD.

In processing step 24, disturbing noise structures in R4BILD are eliminated. R4BILD contains not only ring artefacts, but also noise components, due to the unavoidable pixel noise in CT images. For the suppression of these noise components, advantage is taken of the fact that ring artefacts must be more or less constant on circular arcs of a certain minimum length in order to be recognized as rings at all. The third processing step is thus a low-pass filtering of the pixel values of the image R4BILD along circular arcs around the center of rotation 10. In this way, the ring artefacts are retained, while noise structures are smoothed away. The low-pass filtering can e.g. be realized as a simple averaging. For each pixel P in the image R4BILD with coordinates xp, yp, on the circular arc proceeding through P and around the rotational center 10, having radius $\sqrt{x_P^2+y_P^2}$, the $2N_w+1$ pixels are sought that have angular spacing $-N_w \cdot$SPHI, $-(N_w+1) \cdot$SPHI, . . . $(N_w-1) \cdot$SPHI, $N_w \cdot$SPHI from P. The value SPHI is a freely selectable angular increment. The value of the pixel P is replaced by the average of the $2N_w+1$ pixels. According to their spacing from the center of rotation 10, the pixels are thereby divided (grouped) into pixels in the inner region and pixels in the outer region, in order to enable realization of different angular increments SPHI for the averaging in the inner region and in the outer region. By means of angle rounding, the image WBILD arises from R4BILD. The angle rounding is shown schematically in FIG. 4.

Finally, subtraction of IBILD and WBILD in step 25 yields the result image, in which the ring artefacts are removed.

Figure 3:
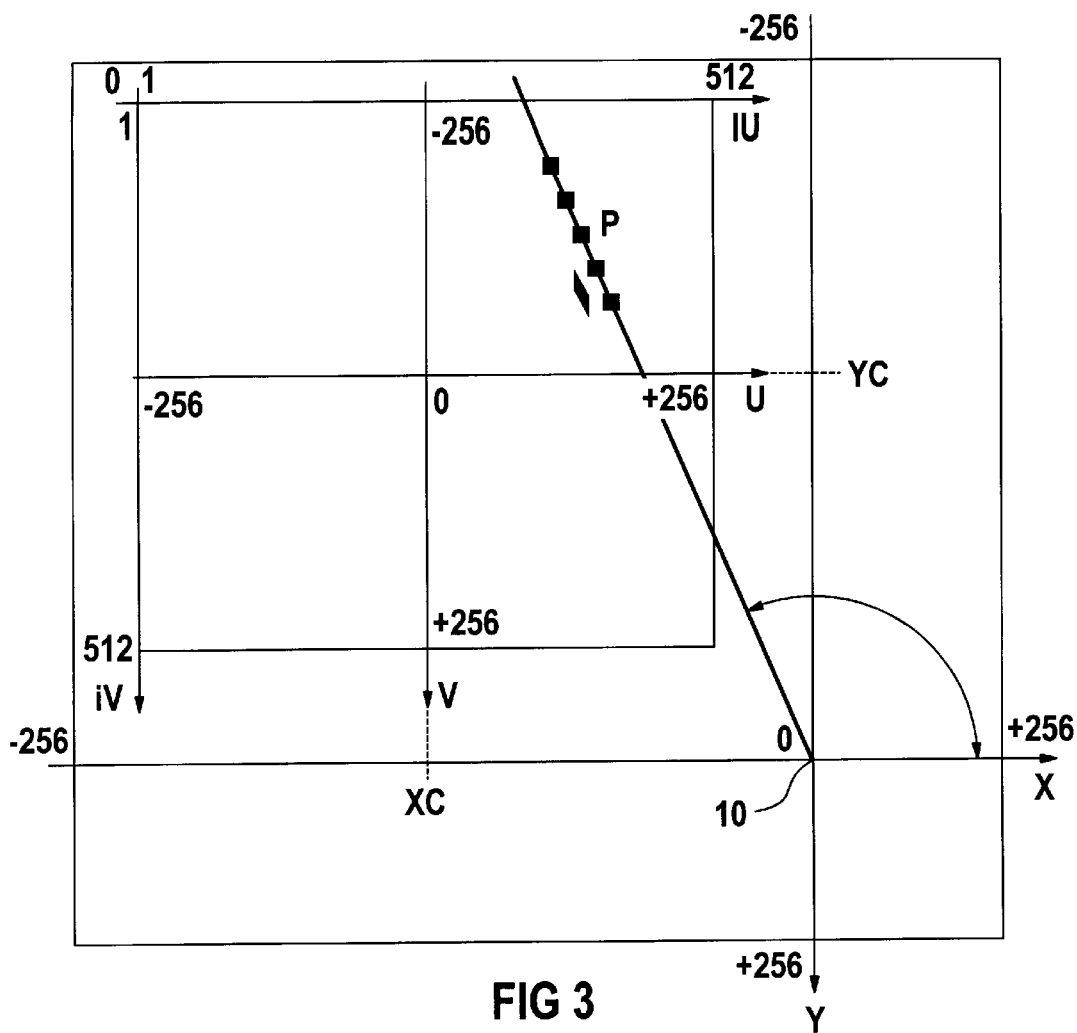
FIG. 3 is a schematic representation of the filtering in the inventive method.

FIG. 3 shows a schematic representation of the above-described first median filtering according to step 18.

Figure 4:
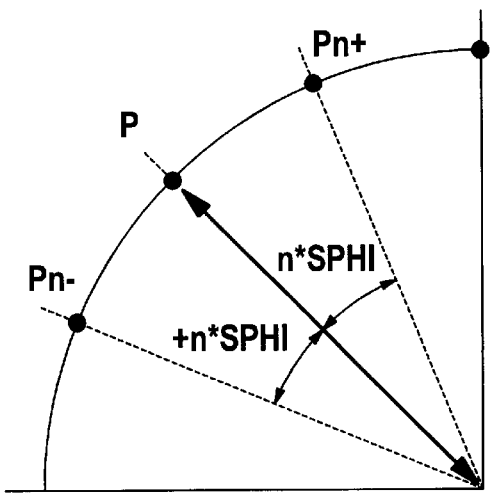
FIG. 4 is a schematic representation for the angle rounding in the inventive method.

FIG. 4 shows a schematic representation of the above-described angle rounding according to step 24.

It is important in the invention that a tomogram of the overall field of measurement, or a segment thereof, is post-processed so that the pixel values of the tomogram are subjected to one or more median filterings and to an averaging, the median filterings and the averaging being conducted along a number of processing directions.

Although various minor modifications might be suggested by those skilled in the art, it should be understood that my wish to embody within the scope of the patent warranted hereon all such modifications as reasonably and properly come with the scope of my contribution to the art.

I claim as my invention:

1. A method for operating a computed tomography apparatus for computerized post-processing of a reconstructed tomogram of a slice of a subject for removing artefacts, comprising the method steps of:

a) obtaining an image matrix IBILD having $N_p \cdot N_p$ pixels, said pixels respectively having CT values, and masking bone and air portions therein by setting all CT values in the pixel matrix greater than a determined threshold SWO equal to SWO, and setting all CT values smaller than a determined threshold SWU equal to SWU, to obtain a new image matrix R1BILD results, also having $N_p \cdot N_p$ pixel values;

b) conducting a median filtering procedure in R1BILD, along a plurality of straight processing lines, all proceeding through a center of rotation of the computed tomography apparatus and, which cover the image matrix R1BILD so that each pixel lies on one of said straight processing lines, by employing a median filter having $2M_1+1$ support points with a spacing $a_{R1}$, to obtain a median-filtered image MED1BILD having pixels with respective values P each resulting from a median value Med of the pixel values of the $2M_1+1$ support points of the image matrix R1BILD;

c) forming of a difference image DIFF1=R1BILD−MED1 BILD for all $N_p \cdot N_p$ pixel values, and conducting of a threshold operation with a artefact threshold $S_{art}$ in the image DIFF1, by setting all pixel values in DIFF1 having a magnitude greater than $S_{art}$ equal to $+S_{art}$ and setting all pixel values in DIFF1 having a magnitude less than $S_{art}$ to $-S_{art}$, to obtain an image R2BILD having pixel values;

d) low-pass filtering the pixel values of the image R2BILD along circular arcs around said center of rotation, by averaging, wherein, for each pixel P in the image R2BILD with coordinates xp, yp on the circular arc around the rotational center that proceeds through P, having a radius $\sqrt{x^2_P+y^2_P}$, the $2N_w+1$ pixels with the angular spacing $-N_w \cdot$SPHI, $-(N_w+1) \cdot$SPHI, . . . $(N_w-1) \cdot$SPHI, $N_w \cdot$SPHI from P are sought, SPH1 being a selected angle increment, and the value of the pixel P is replaced by the average of the $2N_w+1$ pixels, to obtain an image matrix WBILD; and e) subtracting the image matrix WBILD from the image matrix IBILD, a final image in which the ring artefacts are removed.

2. A method for operating a computed tomography apparatus for computerized post-processing of a reconstructed tomogram of a slice of a subject for removing artefacts, comprising the method steps of:

a) obtaining an image matrix IBILD having $N_p \cdot N_p$ pixels, said pixels respectively having CT values, and masking bone and air portions therein by setting all CT values in the pixel matrix greater than a determined threshold SWO equal to SWO, and setting all CT values smaller than a determined threshold SWU equal to SWU, to obtain a new image matrix R1BILD results, also having $N_p \cdot N_p$ pixel values;

b) conducting a first median filtering procedure in R1BILD, along a plurality of straight processing lines, all proceeding through a center of rotation of the computed tomography apparatus and, which cover the image matrix R1BILD so that each pixel lies on one of said straight processing lines, by employing a median filter having $2M_1+1$ support points with a spacing $a_{R1}$, to obtain a median-filtered image MED1BILD having pixels with respective values P1 each resulting from a median value Med1 of the pixel values of the $2M_1+1$ support points of the image matrix R1BILD;

c) forming of a difference image DIFF1=R1BILD−MED1BILD for all $N_p \cdot N_p$ pixel values, and conducting of a threshold operation with a artefact threshold $S_{art}$ in the image DIFF1, by setting all pixel values in DIFF1 having a magnitude greater than $S_{art}$ equal to $+S_{art}$ and setting all pixel values in DIFF1 having a magnitude less than $S_{art}$ to $-S_{art}$, to obtain an image R2BILD having pixel values;

d) forming a difference image $R_3$BILD from the image matrix R1BILD and the image R2BILD for all pixel values $N_p \cdot N_p$;

e) conducting a second median filtering procedure in R3BILD along said plurality of straight processing lines, which cover the image matrix R3BILD so that each pixel is located on one of said straight processing lines, by employing a second median filter having $2M_2+1$ support points with spacing $a_{R2}$, to obtain a median-filtered image MED2BILD having pixels with respective values P2 each resulting from a median value Med2 of the pixel values of the $2M_2+1$ support points of R3BILD;

f) forming a difference image DIFF2=R1BILD−MED2BILD for all $N_p \cdot N_p$ pixel values, and conducting a threshold operation with the artefact threshold $S_{art}$ in the image DIFF2, by setting all pixel values in DIFF2 having magnitude greater than $S_{art}$ and by setting all pixel values in DIFF2 having a magnitude less than $S_{art}$ equal to $+S_{art}$ to $-S_{art}$, to obtain an image R4BILD having pixel values;

g) low-pass filtering the pixel values of the image R4BILD along circular arcs around said center of rotation, by averaging, wherein, for each pixel P2 in the image R2BILD with coordinates xp, yp on the circular arc around the rotational center that proceeds through P2, having a radius $\sqrt{x^2_P+y^2_P}$, the $2N_w+1$ pixels with the angular spacing $-N_w \cdot$SPHI, $-(N_w+1) \cdot$SPHI, . . . $(N_w-1) \cdot$SPHI, $N_w \cdot$SPHI from P2 are sought, SPH1 being a selected angle increment, and the value of the pixel P2 is replaced by the average of the $2N_w+1$ pixels, to obtain an image matrix WBILD; and h) subtracting the image matrix WBILD from the image matrix IBILD, a final image in which the ring artefacts are removed.

3. A computed tomography apparatus having computer means for post-processing a reconstructed tomogram of a slice of a subject for removing ring artefacts, said computer means comprising:

a) Means for obtaining an image matrix IBILD having $N_p \cdot N_p$ pixels, said pixels respectively having CT values, and masking bone and air portions therein by setting all CT values in the pixel matrix greater than a determined threshold SWO equal to SWO, and setting all CT values smaller than a determined threshold SWU equal to SWU, to obtain a new image matrix R1BILD results, also having $N_p \cdot N_p$ pixel values;

b) Means for conducting a median filtering procedure in R1BILD, along a plurality of straight processing lines, all proceeding through a center of rotation of the computed tomography apparatus and, which cover the image matrix R1BILD so that each pixel lies on one of said straight processing lines, by employing a median filter having $2M_1+1$ support points with a spacing $a_{R1}$, to obtain a median-filtered image MED1BILD having pixels with respective values P each resulting from a median value Med of the pixel values of the $2M_1+1$ support points of the image matrix R1BILD;

c) Means for forming of a difference image DIFF1= R1BILD−MED1BILD for all $N_p \cdot N_p$ pixel values, and conducting of a threshold operation with a artefact threshold $S_{art}$ in the image DIFF1, by setting all pixel values in DIFF1 having a magnitude greater than $S_{art}$ equal to $+S_{art}$ and setting all pixel values in DIFF1 having a magnitude less than $S_{art}$ to $-S_{art}$, to obtain an image R2BILD having pixel values;

d) Means for low-pass filtering the pixel values of the image R2BILD along circular arcs around said center of rotation, by averaging, wherein, for each pixel P in the image R2BILD with coordinates xp, yp on the circular arc around the rotational center that proceeds through P, having a radius $\sqrt{x^2_P + y^2_P}$, the $2N_w+1$ pixels with the angular spacing $-N_w \cdot SPHI$, $-(N_w+1) \cdot SPHI$, . . . $(N_w-1) \cdot SPHI$, $N_w \cdot SPHI$ from P are sought, SPH1 being a selected angle increment, and the value of the pixel P is replaced by the average of the $2N_w+1$ pixels, to obtain an image matrix WBILD; and e) subtracting the image matrix WBILD from the image matrix IBILD, a final image in which the ring artefacts are removed.

4. A computed tomography apparatus having computer means for post-processing a reconstructed tomogram of a slice of a subject for removing ring artefacts, said computer means comprising:

a) Means for obtaining an image matrix IBILD having $N_p \cdot N_p$ pixels, said pixels respectively having CT values, and masking bone and air portions therein by setting all CT values in the pixel matrix greater than a determined threshold SWO equal to SWO, and setting all CT values smaller than a determined threshold SWU equal to SWU, to obtain a new image matrix R1BILD results, also having $N_p \cdot N_p$ pixel values;

b) Means for conducting a first median filtering procedure in R1BILD, along a plurality of straight processing lines, all proceeding through a center of rotation of the computed tomography apparatus and, which cover the image matrix R1BILD so that each pixel lies on one of said straight processing lines, by employing a median filter having $2M_1+1$ support points with a spacing $a_{R1}$, to obtain a median-filtered image MED1BILD having pixels with respective values P1 each resulting from a median value Med1 of the pixel values of the $2M_1+1$ support points of the image matrix R1BILD;

c) Means for forming of a difference image DIFF1= R1BILD−MED1BILD for all $N_p \cdot N_p$ pixel values, and conducting of a threshold operation with a artefact threshold $S_{art}$ in the image DIFF1, by setting all pixel values in DIFF1 having a magnitude greater than $S_{art}$ equal to $+S_{art}$ and setting all pixel values in DIFF1 having a magnitude less than $S_{art}$ to $-S_{art}$, to obtain an image R2BILD having pixel values;

d) Means for forming a difference image R3BILD from the image matrix R1BILD and the image R2BILD for all pixel values $N_p \cdot N_p$;

e) Means for conducting a second median filtering procedure in R3BILD along said plurality of straight processing lines, which cover the image matrix R3BILD so that each pixel is located on one of said straight processing lines, b employing a second median filter having $2M_2+1$ support points with spacing $a_{R2}$, to obtain a median-filtered image MED2BILD having pixels with respective values P2 each resulting from a median value Med2 of the pixel values of the $2M_2+1$ support points of R3BILD;

f) Means for forming a difference image DIFF2= R1BILD−MED2BILD for all $N_p \cdot N_p$ pixel values, and conducting a threshold operation with the artefact threshold $S_{art}$ in the image DIFF2, by setting all pixel values in DIFF2 having magnitude greater than $S_{art}$ and by setting all pixel values in DIFF2 having a magnitude less than $S_{art}$ equal to $+S_{art}$ to $-S_{art}$, to obtain an image R4BILD having pixel values;

g) Means for low-pass filtering the pixel values of the image R4BILD along circular arcs around said center of rotation, by averaging, wherein, for each pixel P2 in the image R2BILD with coordinates xp, yp on the circular arc around the rotational center that proceeds through P2, having a radius $\sqrt{x^2_P + y^2_P}$, the $2N_w+1$ pixels with the angular spacing $-N_w \cdot SPHI$, $-(N_w+1) \cdot SPHI$, . . . $(N_w-1) \cdot SPHI$, $N_w \cdot SPHI$ from P2 are sought, SPH1 being a selected angle increment, and the value of the pixel P2 is replaced by the average of the $2N_w+1$ pixels, to obtain an image matrix WBILD; and h) subtracting the image matrix WBILD from the image matrix IBILD, a final image in which the ring artifacts are removed.

* * * * *